(12) United States Patent
Avery et al.

(10) Patent No.: US 6,251,090 B1
(45) Date of Patent: *Jun. 26, 2001

(54) INTRAVITREAL MEDICINE DELIVERY

(76) Inventors: Robert Logan Avery, 659-C Del Parque Dr., Santa Barbara, CA (US) 93103; Jeffrey Kevin Luttrull, 3160 Telegraph Rd., Suite 230, Ventura, CA (US) 93003

( * ) Notice: Subject to any disclaimer, the term of this patent is extended or adjusted under 35 U.S.C. 154(b) by 0 days.

This patent is subject to a terminal disclaimer.

(21) Appl. No.: 09/184,925

(22) Filed: Nov. 2, 1998

Related U.S. Application Data (60) Continuation of application No. 08/904,821, filed on Aug. 1, 1997, now Pat. No. 5,830,173, which is a division of application No. 08/353,804, filed on Dec. 12, 1994, now Pat. No. 5,725,493.

(51) Int. Cl.[7] ............................. A61M 5/00; A61M 35/00
(52) U.S. Cl. .................................. 604/9; 604/294
(58) Field of Search ..................... 604/8–10, 294, 604/502, 521; 424/427; 623/4–6

(56) References Cited

U.S. PATENT DOCUMENTS

| | | | |
|---|---|---|---|
| 3,977,404 | * 8/1976 | Theeuwes | 424/427 |
| 4,553,973 | * 11/1985 | Edgren | 604/892 |
| 5,725,493 | * 3/1998 | Avery et al. | 604/9 |
| 5,830,173 | * 11/1998 | Avery et al. | 604/9 |
| 5,989,579 | * 11/1999 | Darougar et al. | 124/427 |

* cited by examiner

Primary Examiner—Dennis Ruhl
(74) Attorney, Agent, or Firm—Leo F. Costello (57) ABSTRACT

An intravitreal medicine delivery device and method are provided and include an implant device through which a wide variety of beneficial medicines including drugs or other pharmacological agents can be introduced into the vitreous cavity over an extended period of time with only a single initial surgery to implant the device. The device and method minimize the surgical incision needed for implantation and avoid future or repeated invasive surgery or procedures. Additional amounts of the initial medicine can readily be introduced or the medication can be varied or changed, as required. Furthermore, the device and method allow the dosage delivered to the vitreous cavity to be device is constructed so as to filter medicines delivered to the cavity and also avoids damage to or interference with other parts of the eye during implantation or during use.

22 Claims, 5 Drawing Sheets

INTRAVITREAL MEDICINE DELIVERY

This is a continuation application of U.S. patent application Ser. No. 08/904,821 filed Aug. 1, 1997 now U.S. Pat. No. 5,830,173, which is a divisional of U.S. patent application Ser. No. 08/353,804 filed Dec. 12, 1994 and now U.S. Pat. No. 5,725,493.

FIELD OF THE INVENTION

This invention pertains to intravitreal medicine delivery and more particularly to an implant device for delivering medicine to the vitreal cavity of the eye, and to a method for introducing medicines into the vitreal cavity using the device.

BACKGROUND

Within the past several decades, great advances have been made in the diagnosis and treatment of vitreoretinal diseases. Advances in laser technology, and vitreoretinal surgical techniques, have significantly improved the prognosis of numerous retinal conditions including diabetic retinopathy, macular degeneration, and retinal detachment. As the pathophysiology of these and many other vitreoretinal diseases is also becoming more clearly understood, a host of potential pharmacological agents is currently under investigation.

In addition to the numerous antibiotic, antiviral, and antifungal agents currently used to treat infections of the retina and vitreous, many antiinflammatory and anticancer drugs have been shown to be useful in treating diseases such as proliferative vitreoretinopathy. As the role of growth factors involved in diabetic retinopathy, macular degeneration, and other retinal degenerations is elucidated, new classes of agents have been found to be of possible benefit, including growth factors themselves, blocking antibodies to growth factors, antisense oligonucleotides, and even gene therapy with growth factor inserts.

Unfortunately, the delivery of drugs to the retina is often problematic. Most agents given topically to the eye (in the form of eye drops) do not penetrate through the anterior segment of the eye well enough to reach the vitreous or retina in therapeutic concentrations. Medications can be given orally or intravenously, but the blood vessels within the retina (and other parts of the central nervous system) are relatively impermeable to many agents. Furthermore, these drugs may have significant systemic side effects on other organs of the body. Drugs can be directly injected into the vitreous cavity, via a needle passed through the pars plana, and this technique is currently employed to combat certain severe, sight-threatening infections. However, this procedure itself entails certain risks, such as infection, bleeding, cataract formation, and retinal detachment. Furthermore, the majority of the injected drug is often cleared from the vitreous cavity within several days, necessitating multiple injections for prolonged treatment.

Accordingly, devices have been developed for improving the introduction of drugs to the vitreal cavity. One such device is a biodegradable polymer designed to be injected into the vitreous cavity where it slowly releases drug as it dissolves. A similar drug-containing polymer has been developed which is made in the shape of a tack or plug to be surgically inserted into the eyewall at the pars plana so that it projects into the vitreous cavity. Liposomes containing pharmacological agents have been developed to slowly release the agent after injection into the vitreous cavity. Another device is a plastic pellet which contains a retinal drug (ganoclovir) and is sutured inside of the vitreous cavity where the drug slowly dissolves into the cavity.

Although such devices as those briefly referred to above are apparently effective in delivering drugs into the vitreous cavity, they have significant disadvantages. First, all of these devices contain a certain amount of drug which when expended cannot be replenished without repeating the surgical implantation or intravitreal injection. Although these different devices can release drugs for weeks to months (or in the case of the plastic pellet, almost one year), certain indications for intravitreal drug administration require extended or lifetime therapy. Therefore, multiple procedures are often required and are highly undesirable.

Secondly, the device with the longest release rate, the plastic pellet of ganiclovir, requires a very large eyewall incision (5 mm) to implant due to its large size. Although the other devices can be implanted or injected through a smaller incision (1 mm or less), those that are injected freely into the vitreous cavity instead of anchored to the eyewall can migrate within the eye and come in direct contact with the retina where they can block vision or release high local concentrations of drug which could potentially prove toxic to delicate retinal tissue.

Third, many pharmacological agents cannot easily and effectively be incorporated into biodegradable polymers. Furthermore, many potential pharmacological agents would not remain stable for extended periods of time in the vitreous cavity. Therefore, there is a significant limitation to what pharmacological agents can be administered via the slow release devices currently available.

Fourth, since the plug or pellet is in essence the drug itself, treatment is limited to this drug, so that another surgery or procedure is required to change it if administration of a different drug is desired.

SUMMARY

The present invention is directed to intravitreal medicine delivery involving an implant device and method wherein a wide variety of beneficial drugs or other pharmacological agents or medicines can be introduced into the vitreous cavity over an extended period of time, as much as the life of the patient, with only a single initial surgery to implant the device; wherein the surgical incision needed for implantation is minimized; wherein additional amounts of drugs over an initial supply can be introduced without further invasive surgery; wherein the type of medicine can be varied or changed depending on such factors as the disease being treated or drug availability; wherein the dosage of agent being administered is controllable; and wherein damage or interference by the implant to various parts of the eye is avoided.

It is an object of the present invention to provide for improved delivery of drugs and other pharmacological agents to the vitreous cavity of the eye, especially for treating vitreoretinal diseases.

It is another object to enable medicinal agents to be delivered to the vitreous cavity with a single initial surgery and without the need for repeated invasive surgeries or procedures.

It is yet another object of this invention to allow replenishment of the drug or other medicinal agent within an implant attached to the eyewall by injection into the implant through the conjunctivae and not through the eye wall.

It is further object to be able to change the pharmacological agent being dispensed from an eye implant device into the vitreal cavity, without surgery or other invasive procedure.

It is also an object to control the dosage of drugs or other pharmacological agents delivered to the vitreous cavity from an implant device.

It is still another object of the present invention to enable the patient to control delivery of dosages of medicines to the vitreous cavity with a delivery device implanted on the patient's eyeball.

It is a still further object to implant an intravitreal medicine delivery device which dispenses medicine into the vitreous cavity without interference with or damage to various parts of the eye.

It is yet another object of the present invention to prevent inadvertent puncture of the eyeball by an injection needle used to replenish the supply of drugs or other agents in an eye implant device.

It is also an object of the subject invention to prevent an uncontrolled movement of medicines into the vitreous cavity from an intravitreal delivery implant when the supply of medicines in the implant is being replenished in situ.

It is another object of this invention to filter medicines being dispensed from an implant device before being admitted to the vitreous cavity thereby to prevent unwanted particulate matter, such as undissolved biodegradable polymer, from moving into the cavity, while allowing medicines to pass into the cavity.

It is a feature of the present invention to have a relatively large drug or other medicine-containing reservoir which is located outside the eyewall in the sub-conjunctival space and which is connected to the vitreous cavity by a smaller tube through the pars plana so that a substantial amount of medicine can be brought into the vitreous cavity with a minimum of eyewall incision.

It is a feature of this invention to provide an intravitreal medicine delivery device with a pump for moving predetermined doses of drugs or other agents into the vitreous cavity and which can be operated by the patient.

It is another feature to provide an intravitreal drug delivery device which has a low profile for closely-fitting implantation under the conjunctiva and Tenon's capsule of the eyeball.

It is another feature of this invention to provide an eye implant device with an injection port which can be readily identified through overlying tissue for injecting an additional supply of medicine into the implant device.

It is still another feature of this invention to suture a medication delivery implant device to the eyewall so that it facilitates subsequent injections of medication into it while maintaining its implanted position.

These and other objects, features, and advantages of the subject invention will become apparent upon reference to the accompanying drawings, the following description, and the appended claims.

DESCRIPTION OF THE DRAWINGS

FIG. 12a–12e are schematic views showing the sequence of positions of the valve of FIGS. 10 and 11.

DETAILED DESCRIPTION

Intravitreal Medicine Delivery Device—First Embodiment

Figure 1:
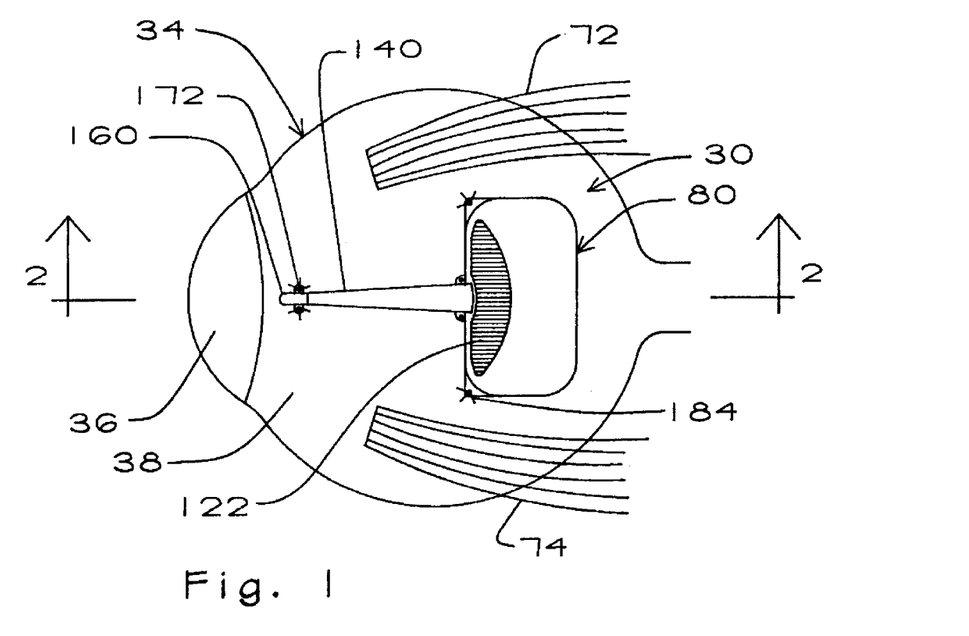
FIG. 1 is a plan view of one embodiment of an intravitreal medicine delivery device according to the present invention shown implanted on a human eyeball, which is schematically shown, it being understood that both the device and the eyeball are enlarged from actual size.
Figure 2:
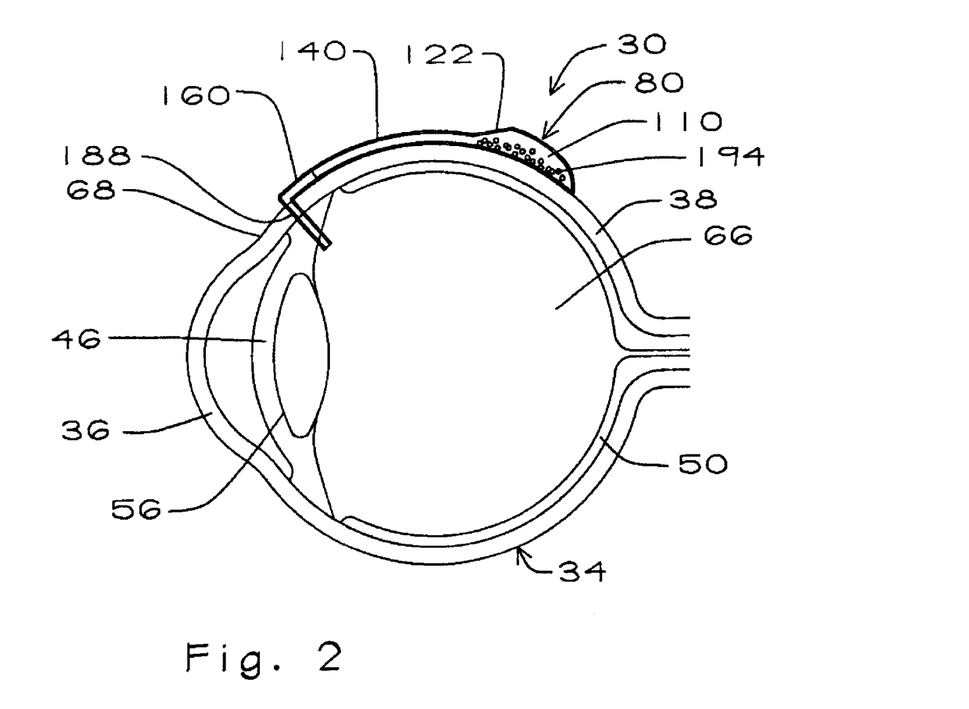
FIG. 2 is a cross-section taken along line 2—2 of FIG. 1.

The first embodiment of an intravitreal medicine delivery device of the present invention is identified in FIGS. 1–6 by the numeral 30 and is shown in FIGS. 1 and 2 as being implanted on a human eyeball or globe 34. The eyeball is shown schematically and in just enough detail to enable an understanding of the present invention. Certain parts of the eye are thus briefly identified with reference numerals. Schematically represented in either or both of FIGS. 1, 2, 8 and 9 are the cornea 36, the sclera 38, the conjunctiva and Tenon's capsule 44, the iris 46, the retina 50, the lens 56, the eyelid 60, eyelashes 62, the vitreous cavity 66, the pars plana 68, the superior rectus muscle 72, and the lateral rectus muscle 74.

Figure 17:
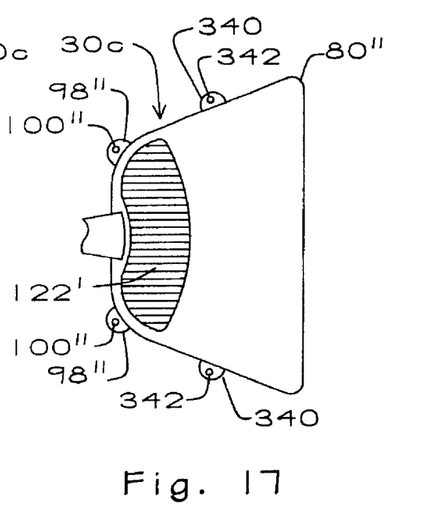
FIG. 17 is a plan view of a portion of the subject delivery device but depicting still another embodiment of the housing.

The first embodiment of the intravitreal delivery device 30 is shown in detail in FIGS. 3–7 and is now described. The device includes a housing 80 most of which is preferably pre-formed of semi-rigid material to have a concavo-convex shape and a low profile so as during surgery to fit easily and closely against an eyeball, as 34. In plan view the housing preferably has a generally rectangular outline (FIG. 4) or a trapezoidal outline (FIG. 17) but this outline may be varied to facilitate implantation as will be understood by those skilled in the art.

The housing 80 (FIGS. 3–6) has a base or bottom wall 84 which has an outwardly, spherically concave shape or curvature generally complementary to the curvature of the eyeball 34. This bottom wall is made of a tough material impenetrable by an injection needle or syringe and is preferably of a plastic, such as nylon, Kevlar, or polymethyl methacrylate (PMMA), but may be made of metal, such as tantalum. The housing also has a top or upper wall 86 which has an outwardly spherically convex shape and is joined in a fluid-tight manner to the bottom wall along a peripheral edge 90. The top and bottom walls may be one-piece and integral along the edge or of two different pieces sealed along the edge. This edge has an anterior segment 92, a posterior segment 94, and lateral segments 96 and 97 which meet at four corners of the housing. Outer corner fixation tabs 98 project from the anterior corners of the housing and have suture-receiving eyelets 100. Spaced, inner anterior fixation tabs 102 project from the anterior segment 92 and also have suture-receiving eyelets 104.

The spaced top and bottom walls 86 and 84 (FIGS. 5 and 6) provide a fluid-tight storage reservoir or chamber 110 in the housing 80. This reservoir has a maximum height dimension indicated by the numeral 112 and measured radially of the curved top and bottom walls and where the spacing between the walls is the greatest. As an example but not limiting to the invention, this maximum height dimension is preferably about 3–4 mm. Of course, the height of the reservoir tapers downward toward all four segments 92, 94, 96 and 97 (FIGS. 3, 5 and 6) of the edge 90. It is also noted that the lateral dimensions of the reservoir, that is the length and width dimensions, measured generally spherically of the walls, are relatively much greater than the maximum height. For the embodiment shown in FIG. 4, but again not limiting to the invention, the width or distance between lateral edges 96 and 97 is approximately 1.5 cm and the length or distance between the anterior and posterior edges 92 and 94 is approximately 1 cm.

Of particular significance, however, is that the top wall 86 (FIGS. 3–6) of the housing 80 has a slightly uplifted, arcuate, anterior medicine-injection port or area 122 closely adjacent to the anterior edge 92 and having opposite ends 123 closely adjacent to the anterior corners of the housing. The top wall also has a main or remainder portion 124 of greater area than the injection port. This main portion is of the same material as the bottom wall 84 and is the part of the top wall which is joined to the bottom wall. Thus, this main portion is needle-impenetrable and fluid-impervious.

The injection port 122 (FIGS. 3–6), however, is of a material, such as silicone rubber, which is penetrable by a needle or syringe but which reseals itself when the needle is withdrawn so that the port is normally fluid-impervious. An important feature of the port is that the material thereof is colored, for example, blue, as indicated in the drawings. This coloration is important to provide a marker or identification mark which is visible exteriorly of the eye, especially through covering tissue or patches, to facilitate location of the port by attending medical personnel.

The reservoir 110 (FIGS. 5 and 6) has an anterior fluid outlet 130 located in the top wall 86 of the housing 80 between the anterior segment 92 and the injection port 122 and is thus between the inner tabs 102. A filter 134 is optionally mounted in the outlet to prevent particulate materials, such as biodegradable polymer, from passing out of the reservoir and into the vitreous cavity, while permitting medicines released from the dissolving polymers to pass out of the reservoir 110 and into the cavity. This filter may take various forms such as a semi-permeable, osmotic membrane or a porous cellulose filter such as a Millipore filter. Furthermore, it may be a thin capillary tube, or coil of capillary tube, designed to restrict the flow of drug-containing fluid from the reservoir 110 into the vitreous cavity 66.

Figures 3, 4, 5, 6, 7:
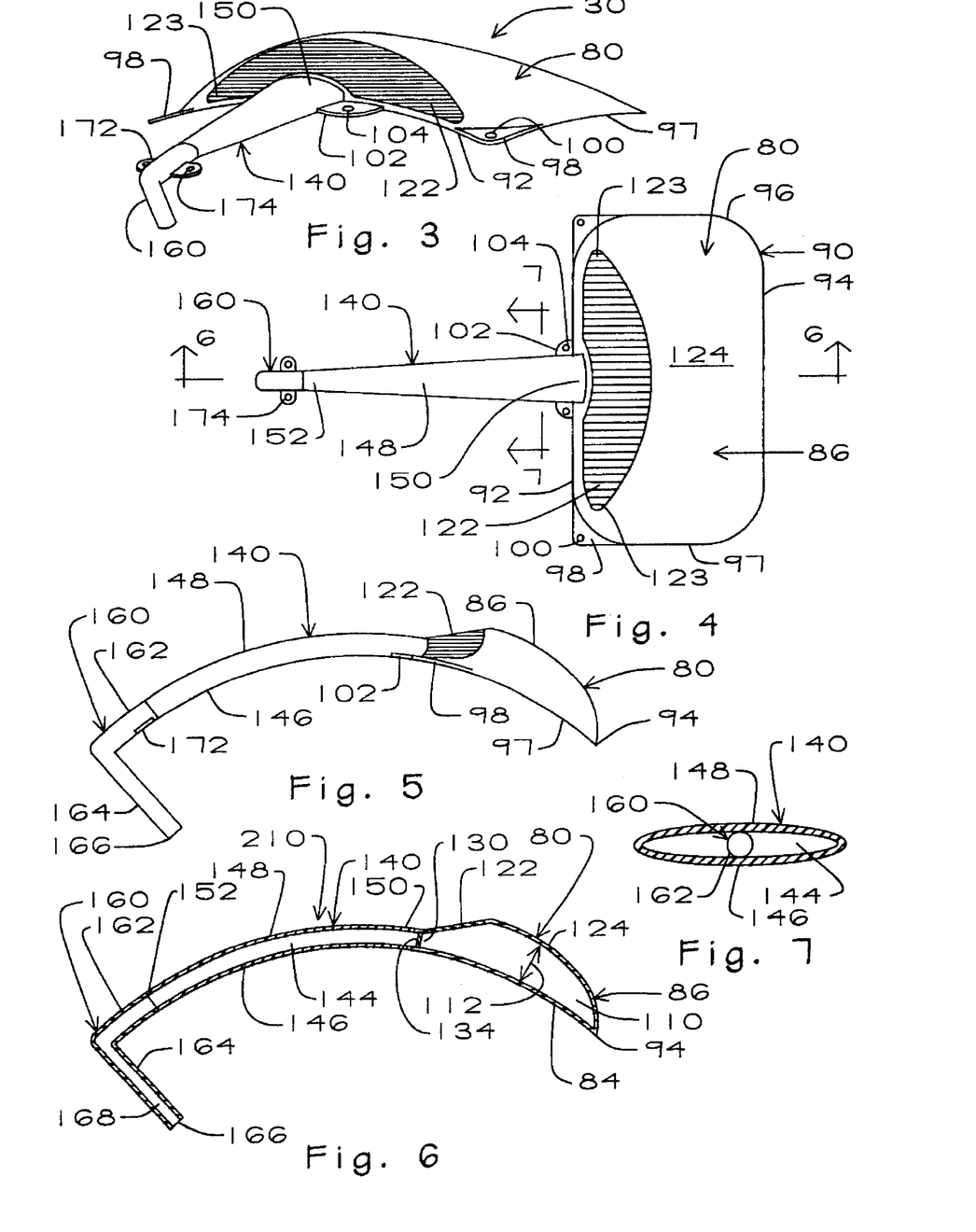
FIG. 3 is an isometric view of the subject intravitreal medicine delivery device, even further enlarged from the size in FIG. 1 and showing the three principle parts of the device, namely, a housing, a tube, and an elbow.
FIG. 4 is a plan view of the intravitreal medicine delivery device shown in FIG. 3.
FIG. 5 is a side elevation of the device shown in FIG. 4.
FIG. 6 is a cross-section along line 6—6 of FIG. 4.
FIG. 7 is a cross-section along line 7—7 of FIG. 4.
Figure 8:
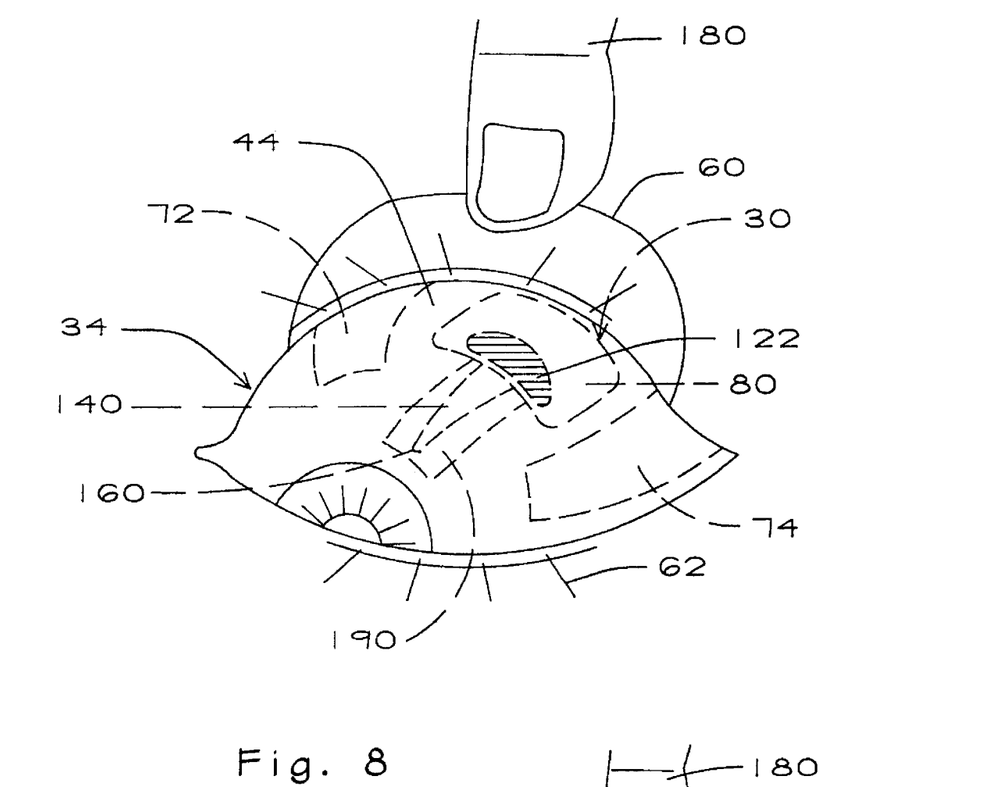
FIG. 8 is a greatly enlarged schematic view of an eye showing the subject intravitreal medicine delivery device implanted on the eyeball and representing the eyelid being lifted to expose the region of the eye where the implant is located.

The subject intravitreal medicine delivery device 30 also includes a tapered, elongated delivery tube 140 (FIGS. 3–7) of fluid-impervious compressible elastomeric material, such as a silicone elastomer, thus providing a fluid passageway or lumen 144. Preferably, the tube is of oval cross-section as illustrated, but is not limited to this cross-section. The tube has a low or flat profile, like the housing, and includes a base and upper walls 146 and 148 which are joined at lateral edges. The passageway has a relatively small minor axis or dimension, as best seen in FIG. 7, which is preferably less than the height maximum height dimension 112 of the reservoir 110. Again, although not limiting to the invention, this minor axis is preferably about the size of a 19–20 gauge lumen. The base wall may be outwardly convex, as shown, or concave to conform to the curvature of the eyeball. Significantly, the top wall is resiliently compressible toward the base wall by applying slight digital pressure against the wall to constrict the passageway. When the pressure is relieved, the top wall returns to its normally relaxed position with the passageway fully open.

The tube 140 (FIGS. 3–7) has a relatively wide proximate end 150 connected to the housing 80 around the outlet 130 so that the passageway 144 is in fluid communication with the reservoir 110. In effect, the passageway is an extension of the reservoir so that the reservoir and the passageway together constitute one large storage reservoir or chamber. The tube converges anteriorly from the housing to a relatively narrow distal end 152, it being noted that the major axis of the passageway thus varies from a maximum at the proximate end to a minimum at the distal end. As shown in FIGS. 5 and 6, the tube is preferably preformed with, and has sufficient rigidity to maintain, a longitudinal curvature complementary to the curvature of an eyeball, but is sufficiently flexible to allow limited flexing at the juncture of the tube and the housing.

The subject delivery device 30 (FIGS. 3–6) also includes a semi-rigid tubular elbow 160 having an in-line connector sleeve 162 attached to the distal end 152 of the tube 140 and an intravitreal extension 164 which projects from the sleeve at an angle to the in-line sleeve, preferably of about eighty to ninety degrees, and terminates in a tip 166. The sleeve is of about the same diameter as the minor axis or height of the tube, as best seen in FIG. 7, and although given by way of example only, is about 19–20 gauge. The elbow thus provides a lumen or fluid passageway 168 in fluid communication with the passageway in the tube and opening at the tip. Another pair of fixation tabs 172 project laterally from the sleeve 162 of the elbow 160 and have suture eyelets 174. The elbow may be made of the same material as the housing.

Once again, to provide an example of a preferred embodiment of the intravitreal delivery device 30 (FIG. 4) but not limiting to the invention, the length of the combined tube 140 and elbow 160, from the anterior segment 92 to the bend of the elbow, is about 7 mm, and the maximum transverse dimension of the tube at its proximate end is about 3 mm.

Intravitreal Medicine Delivery Method

The method of the present invention and use of the subject delivery device 30 are best described by reference to FIGS. 1, 2, 8 and 9. The delivery device is implanted within the socket of the eye on the episcleral surface of the globe (eye wall) 66 by placing the device under the conjunctiva 44 and Tenon's capsule. The device is located between the superior and lateral rectus muscles 72 and 74 with the base wall 84 fitted against the eyeball 34 and the anterior edge 92 located posteriorly of the muscle roots and slightly posteriorly of the equator of the eyeball, as best seen in FIG. 1. Thusly located, the injection port 122 faces anteriorly, and the tube 140 projects anteriorly with the tip 166 at the pars plana 68.

A hole 188 (FIG. 2) of about 1.0 mm is incised through the eyeball 34 at the pars plana 68 and into the vitreous cavity 66. The intravitreal extension 164 of the elbow 160 is inserted through the hole so that it projects into the cavity a distance of preferably approximately 4 mm. In this regard, it is to be noted that the rigidity of the elbow allows the position of the intravitreal extension 164 to be controlled as it is inserted into the cavity so as to avoid contact of the tube with the lens 56, cornea 36 or iris 46. The device 30 is then attached to the episclera 38 with sutures 184 (FIG. 1) in selected eyelets 100 (and/or 104) and eyelets 174 (FIG. 4). The tabs 98 and 102 are provided as alternates in case one location or the other is preferred for the sutures. After suturing the device in place, a sceral patch or graft 190 (FIG. 8) is sutured over the tube 140 for the purpose of preventing of erosion of the implant tube through the conjunctiva, which could lead to infection and require removal of the implant. The rigidity of the elbow and its attachment to the sclera (FIGS. 1 and 2) maintain the intravitreal extension of the implant tube in the position in which it is initially placed so that it does not move around in the cavity as the implant is worn and used by the patient.

A supply of medicine 194 (FIG. 2) is placed in the reservoir 110 before or after implantation. Examples of drugs that may be used are antivirals, antibiotics, steroids, growth factors or inhibitors, anti-sense oligonucleotides, mediators of gene therapy, and others. These may be in the form of fluids, solids, suspensions, emulsions, slow-release or time-release beads, capsules, liposomes, ion-exchange beads, biodegradable polymers, pellets, or other microparticulate vehicles. As an example, the medicine 194 is shown as time-release beads in FIG. 2.

If drugs or other agents are injected after the implant surgery, the eyelid 60 remains lifted (FIG. 8) to expose the region where the device 30 is implanted. Because of its color, the injection port 122 is visible through the conjunctiva tissue 44 covering the device. The tube 140 may be depressed to block the passageway 144 (FIG. 6), and an injection needle 202 of a syringe 200 (FIG. 9) filled with the medicine 194 penetrates the port, and the medicine is injected.

If a large volume of medicine 194 is to be instilled into the reservoir 110 (FIG. 9), either initially or to refill the implant 30 at a later date, venting of the implant reservoir by a second needle, not shown but placed through the injection port 122 simultaneously with injection, may be required. Injection of small volumes of medicine into the reservoir, however, may not require venting.

After the injection is completed (FIG. 9), the needle 202 is withdrawn and the tube 140 is released to expand to normal size (FIG. 2). By blocking the passageway during filling of the reservoir, fluid flow or fluid pressure through the tube and elbow 160 and into the vitreous cavity 66 is precluded. When the needle is withdrawn, the port 122 reseals itself.

Following the implant surgery and as the patient wears the implanted device 30 (FIG. 2), the medicine 194 is thus exposed to the vitreous cavity 66 over an extended period of time. Whether the medicine is in the form of solid material from which the medicine diffuses or whether the medicine is fluid-borne, this exposure through the passageways 144 and 168, allows the medicine to diffuse, flow or otherwise move or pass from the reservoir 110 into the vitreal cavity.

The impetus for diffusion of the medicine 194 from the reservoir 110 into the vitreous cavity 66 occurs for several reasons. First, the concentration gradient between the medicine in the reservoir and vitreous fluid will set up its own diffusion gradient causing a movement of medicine into the cavity. Secondly, the patient can cause frank fluid flow by digitally pressing against the eyelid 60 and thereby against the top wall 148 of the tube 140 to force fluid-borne medicine into the vitreous cavity. Thus, the compressible top wall 148 in combination with the storage reservoir and passageways 144 and 168 may serve as a pump which is generally identified by numeral 210. Thirdly, injection of medicine via reservoir increases pressure in the reservoir driving a net flux of fluid through the tube into the vitreous cavity. Finally, normal physiologic forces, such as blinking, eye movements, and normal blood pressure pulses, will cause small pressure gradients to develop in the implant tube promoting passage of medicine into the vitreous cavity.

Figure 9:
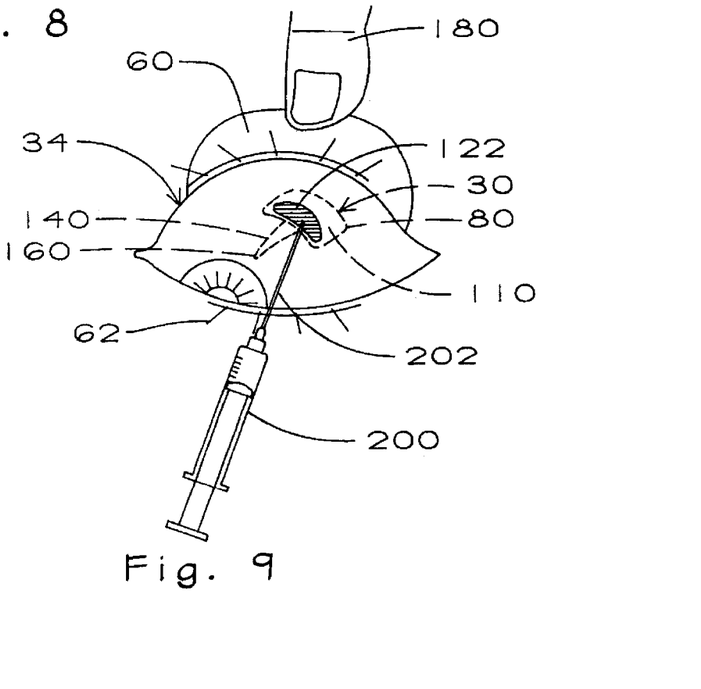
FIG. 9 is similar to FIG. 8, still enlarged but on a smaller scale, and demonstrating how the injection port of the subject device can be readily identified through overlying tissue.

This movement of medicine 194 (FIG. 2) from the storage reservoir 110 into the vitreous cavity 66 will normally continue, or be forced to flow by the patient's pumping of the tube 140, for an extended period of time whereupon it may be necessary to replenish the original supply of the medicine. Also, because of the discovery of a new and better drug or the need for a different drug or other medicine, it may be desirable to change the medication. In any case, the patient returns to the physician's office for the following simple procedure. The eyelid 60 is lifted (FIGS. 8 and 9) and the patient looks down to expose the region of the implanted delivery device 30. The scleral patch 190, the conjunctiva and Tenon's capsule 44 and a fibrous capsule (not specifically shown in the drawings but believed to be well understood), which grows over the device under the conjunctiva obscures the device 30, except for the injection port 122, as illustrated in FIG. 9. The port is visible through the tissue because it is identified with a color which can be seen through the tissue.

While digitally compressing the tube 140 (FIGS. 8 and 9) to block the passageway 144, as previously described, the injection port 122 is penetrated with the syringe needle 202 and a new supply of medicine 194 is injected into the reservoir 110. As previously indicated, venting of the implant reservoir 110 may be required for injection of larger volumes of medicine. Pressure on the tube is released and the needle is withdrawn, the port sealing after the withdrawal. The intravitreal delivery device 30 is then capable of repeating its delivery of medicine to the vitreous cavity 66 over an extended period of time, as previously described. Of prime significance, a repeat surgery to re-introduce a new implant, or another invasive procedure to inject a supply of medicine, is avoided.

A significant relationship between the location of the suturing tabs 98, 102, and 172 and the injection port 122 is to be noted. With reference to FIG. 1, it will be seen that all the sutures 184 are located anteriorly of the port. Thus, when the injection needle 202 (FIG. 9) presses against the port to thrust the needle through the port, the sutured tabs resist posterior movement of the implant device, as 30, and maintain it in its implanted position.

Intravitreal Delivery Device—Second Embodiment

Figure 11:
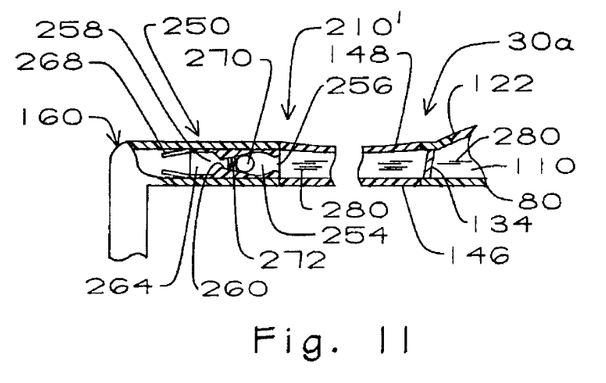
Figure 12:
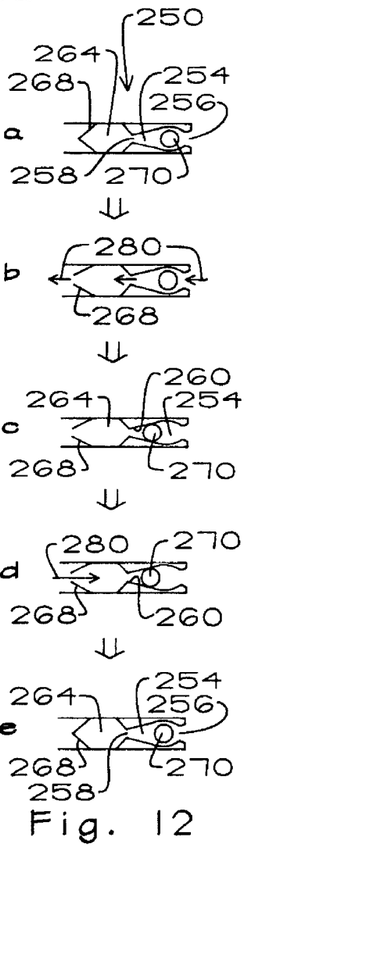

The second embodiment 30a (FIGS. 10–12) of the present invention is the same as the first embodiment except that a valve 250 is incorporated in the elbow 160 to enhance the pumping action previously described. The valve shown and described is a ball-check valve, but other valves having a similar function can be employed. The valve shown, however, includes a valve body 252 fitted in the connector sleeve 162. The valve body provides an outer chamber 254 having an annular inlet 256 opening into the passageway 144 of the tube 140, an annular outlet 258 opening toward the intravitreal extension 164, an annular valve seat 260 between the inlet and outlet, and a dosage chamber 264 between the valve seat and the outlet. The valve also includes a resiliently expandable, conical mouthpiece 268 of a suitable elastomeric material whose apex is normally closed in its relaxed condition but which opens when fluid pressure inside the valve body, in the direction of the apex, forces it open. Still further, the valve includes a resilient ball 270 in the outer chamber and a spring 272 between the ball and the valve seat.

Figure 10:
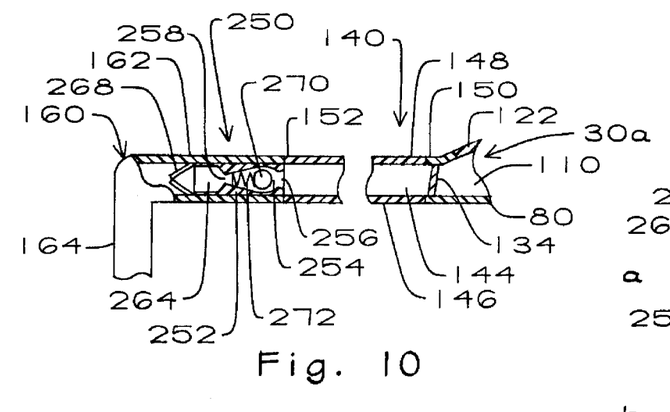
FIGS. 10 and 11 are both cutaway, sectional views of a portion of the intravitreal medicine delivery device of the present invention illustrating a valve in the elbow, with FIG. 11 showing the valve in a different position from FIG. 10.

In operation of the intravitreal delivery device 30a when it incorporates the valve 250 (FIGS. 10–12), the storage reservoir 110 is filled with fluid-borne medicine, as represented by the numeral 280, either during initial manufacture or by subsequent injection through the injection port 122. With reference to the flow diagrams of FIGS. 12a–12e, the condition of the valve in its resting state is shown in FIG. 12a wherein the ball 270 floats in the outer chamber 254 being held away from the seat 260 by the spring 272 (FIG. 10). Because of the pressure gradients previously described in regard to the first embodiment, fluid-borne medicine from the reservoir fills not only the passageway 144 but also the outer chamber 254 (FIG. 11) and the dosage chamber 264. Under these conditions, there is insufficient pressure to open the mouthpiece 268.

When a dose of medicine 280 is to be delivered to the vitreous cavity 66, the patient or attendant presses against the patient's eyelid 60 thereby pressing against the tube wall 148 (FIG. 11) compressing the tube 140 and constricting the passageway 144 and exerting a fluid pressure toward the vitreous cavity 66 (FIG. 12b). This pressure increase is sufficient to force the ball 270 against the spring 272 until the ball seals (FIG. 12c) against the seat 260 thereby temporarily blocking fluid flow through the valve. Such pumping action thus causes a limited quantity of fluid, essentially the amount in the dosage chamber 264, that is, the predetermined dose or aliquot, to flow into the vitreous cavity 66. Thus, the valve 250 and the tube 140, working in cooperative relationship with the reservoir 110 and the elbow 160, constitute a pump 210'.

When pressure on the eyelid 60 and thus the tube wall 148 is relieved (FIGS. 12d and 12e), a reverse pressure develops because of the lowering of pressure in the passageway 144, whereby the valve ball 270 unseats, and the mouthpiece 268 collapses to its closed position. Fluid pressure in the device then returns to an equilibrium state and the valve returns to its resting state, as shown in FIG. 12e.

Intravitreal Delivery Device—Third Embodiment

Figure 13:
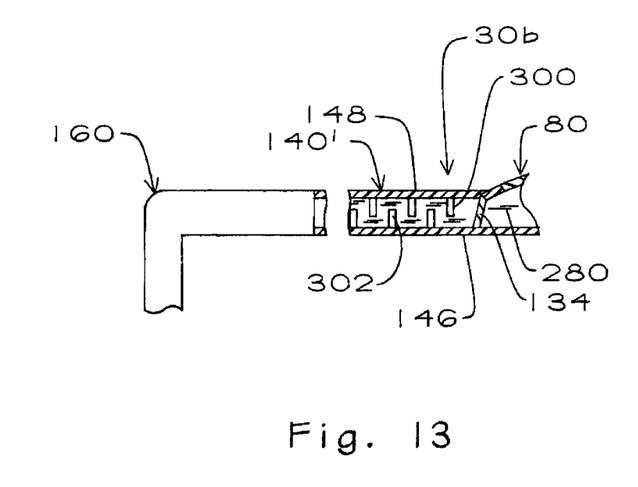
FIG. 13 is a cutaway sectional view of a portion of the subject delivery device and showing an optional feature in the tube of the device.

The third embodiment 30b of the present invention is the same as the first embodiment 30 except as follows. In FIG. 13, there is illustrated a tube 140' connected to the housing 80 and the elbow 160. A series of upper and lower baffles 300 and 302 are respectively attached to the top and base walls 148 and 146 of the tube and project into the passageway 144 in interdigitated, spaced relationship. Since the tube is oval, the baffles are semi-oval or semi-elliptical, but if a tube has a different cross-section, the shape of the baffles would be changed to conform. For example, if the tube is circular, the baffles would be semi-circular. The purpose of these baffles is to facilitate closure of the passageway when the walls of the tube are compressed during filling the storage reservoir 110, while allowing flow through the passageway at all other times when the tube is in normally fully expanded or open condition.

Intravitreal Delivery Device—Fourth Embodiment

Figure 14:
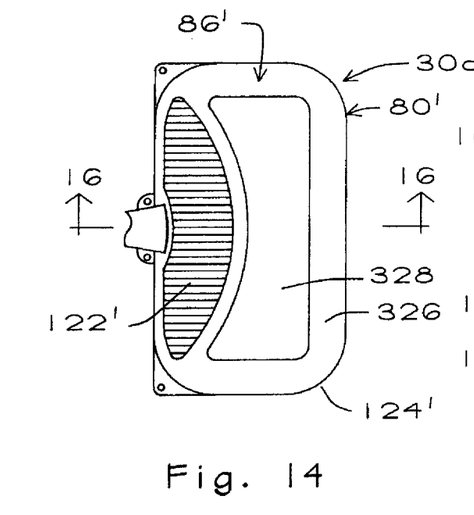
FIG. 14 is a plan view of a portion of the subject medicine delivery device, but depicting another embodiment of the housing of the device.

The fourth embodiment of the delivery device is identified by the numeral 30c and relates to a different housing construction but is otherwise the same as the first embodiment 30. In FIG. 14, there is shown a housing 80' enclosing a reservoir 110' which is in communication with a tube, such as 140 or 141', which is only partially shown in FIGS. 14–16 since this embodiment does not involve a modification of the tube. The modified housing 80', however, has a base wall 84' like the base wall 84 (FIG. 6) and injection port 122' like the injection port 122 (FIGS. 3–6), but a top wall 86' different from the top wall 86 (FIG. 4). The top wall 86' (FIG. 14) has a main portion 124' including a peripheral section 326 and a medial section or roof 328 located posteriorly of the injection port 122'.

Figure 15:
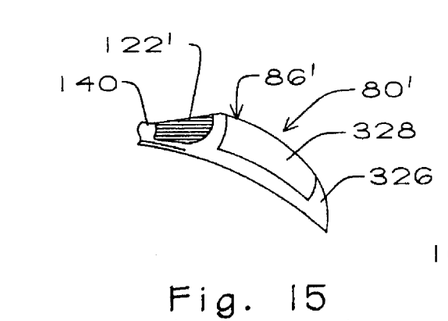
FIG. 15 is a side elevation of the embodiment of FIG. 14.
Figure 16:
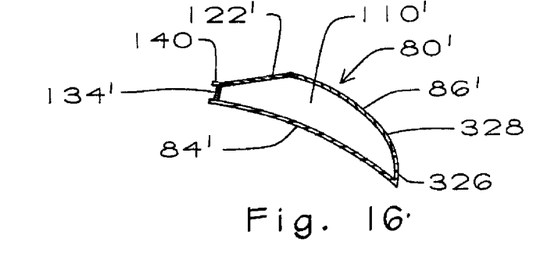
FIG. 16 is a cross-section along line 16—16 of FIG. 14.

As best shown in FIGS. 14 and 15, the peripheral section 326 (excluding the injection port 122') is made of relatively rigid, impenetrable material, such as described for the base wall 84 and the main portion 124 of the first embodiment 30. The injection port 122' is constructed of the same penetrable, resealable material as the port 122. The medial section 328, however, is made of a softer, flexible and resilient material, such as silicone rubber, to allow the medial section or roof to be compressed and thereafter expand to its relaxed state. In addition, this medial section may be semi-permeable to preclude a vacuum from developing in the reservoir when the tube 140 or 140' is compressed while minimizing any appreciable loss of fluid-borne medicine.

Alternatively, the medial section 328 may be made of an elastomeric material which is distended by the injection of a large volume of medicine into the reservoir 110' via the injection port 122'. The distention of the medial section increases the pressure in the reservoir and forces drug-containing fluid into the tube 140 or 140' where egress into the vitreous is controlled by passage through a filter or capillary tube 134'. Still further, the entire housing 80' may be made of elastomeric material to provide such pressure by distention of the housing.

Intravitreal Delivery Device—Fifth Embodiment

The fifth embodiment (FIG. 17) involves a differently shaped housing 80", to which reference was previously made. Instead of the housings 80 or 80', each of which has a generally rectangular periphery, the housing of this embodiment has a generally trapezoidal outline in plan view. Such a trapezoidal shape may be preferred to facilitate implantation. The trapezoidal housing has an injection port 122", anterior tabs 98" with suture eyelets 100", and lateral tabs 340 with suture eyelets 342. Again, by way of example only, the preferred dimensions of the trapezoidal housing are similar to the rectangular housing except that the posterior edge is about 1.5 cm and the anterior edge is about 0.75 cm.

Intravitreal Delivery Device—Additional Feature

Figure 18:
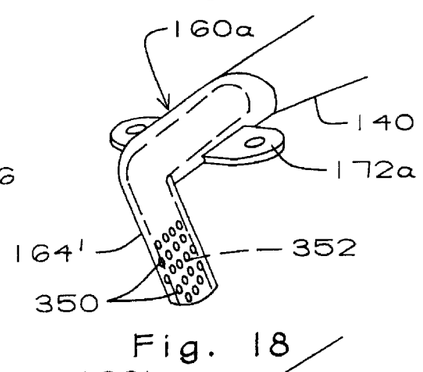
FIG. 18 is an isometric view of another embodiment of an elbow of the subject delivery device which differs from the elbow shown in FIG. 3.
Figure 19:
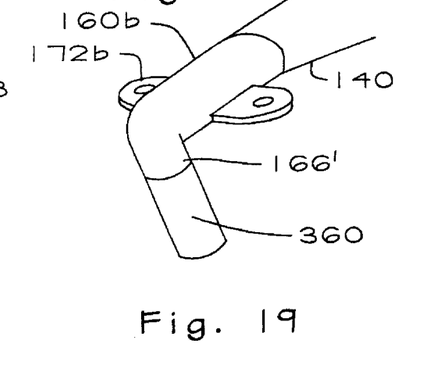
FIG. 19 is also an isometric view of still another embodiment of the elbow.

An additional feature which may be incorporated in the previously described embodiments of the present invention has two species as shown in FIGS. 18 and 19. In FIG. 18, there is illustrated a tubular elbow 160a having an intravitreal extension 164' in which is provided a plurality of holes or slits 350. A semi-permeable wick, insert, or filter 352 of very flaccid material, such as a silicone sponge, is positioned in the passageway of the extension.

In FIG. 19, a semi-permeable membrane or filter 360 in the shape of a relatively rigidly-formed cup is attached to the open tip 166' of a tubular elbow 160b and projects therefrom.

When either species shown in FIGS. 18 and 19 is incorporated in the intravitreal delivery device 30, 30a or 30c of the present invention, medicine passes from the reservoir 110 through the passageways 144 and 168 and through the wick 352, or the membrane 360, from which it diffuses into the vitreous cavity 66. The wick or membrane is optionally used to obviate the possibility of occlusion of the drug passage into the vitreous cavity by particulate matter from the reservoir.

From the foregoing description of the intravitreal medicine delivery device 30, 30a, 30c and method of the present invention, it will be understood how the device and method result in numerous advantages and provide solutions to various problems experienced by prior art devices and methods. The subject invention enables a wide variety of drugs and other pharmacological agents and medicines to be introduced into the vitreous cavity over the lifetime of the patient with only a single initial surgery and with minimum intraocular invasion to implant the device.

Thereafter, to resupply the device 30 with more medicine or to change the medicine, only a simple injection into reservoir 110 through the specially identifiable injection port 122, 122', or 122" of the device is necessary. No invasive surgery or procedure is needed.

As contrasted with biodegradable polymer pellets directly implanted into the eyeball and which do not lend themselves to many potential pharmacological agents, the subject device 30 is not so limited and can utilize the broad range of medicinal agents now available or becoming available. Moreover, the device 30 and method allow the dosage delivered to the vitreous cavity 66 to be controlled and furthermore, allows the patient to control the timing of the deliveries. Additional features incorporated into the device filter the medicine before it enters the vitreous cavity. Also, the device is designed to facilitate its implantation so that it fits closely and relatively comfortably against the eyeball and so that damage or interference with other parts of the eye are avoided.

Although preferred embodiments have been shown and described, various modifications and substitutions may be made thereto without departing from the spirit and scope of the invention. Accordingly, it is to be understood that the present invention has been described by way of illustration and not limitation.

What is claimed is:

1. An intravitreal medicine delivery device for delivering medicine to the vitreal cavity of an eye having an eyeball covered by conjunctiva, comprising a reservoir for holding a supply of medicine, the reservoir having a medicine outlet, means for enabling passage of medicine from the outlet into the vitreal cavity of the eye, and means for attaching the device to the eye so that the entire device is implanted under the conjunctiva.

2. The device of claim 1 wherein the reservoir has a portion through which the reservoir can be filled while the reservoir and the outlet both remain under the conjunctiva.

3. The device of claim 2 wherein the reservoir filling portion is capable of being visible through the conjunctiva when the device is implanted.

4. The device of claim 1 wherein the reservoir includes a pump that enables medicine to be pumped into the vitreal cavity through the outlet.

5. The device of claim 4 wherein the pump includes a valve which allows fluid-borne medicine to flow from the reservoir into the vitreal cavity but restricts fluid flow from the vitreal cavity into the reservoir, and wherein the outlet has a compressible and expandable portion that is part of the pump and which upon expansion draws fluid-borne medicine from the reservoir and upon compression, forces fluid-borne medicine into the vitreal cavity.

6. The device of claim 1 wherein said reservoir includes a relatively low-profile housing having an eyeball-shaped, spherical curvature adapted to fit closely against the eyeball under the conjunctiva and Tenon's capsule, said reservoir having a minimal height dimension measured radially of said curvature and lateral dimensions measured spherically of the housing and being substantially greater than the height dimension, said outlet including a tube projecting from the housing and having an angular extension for projecting into the vitreal cavity.

7. The device of claim 6 wherein the housing has a medicine injecting port facing outwardly from the housing in the same direction that the tube projects from the housing.

8. The device of claim 1, wherein the outlet includes a fluid passageway having a proximate end in communication with the reservoir and a distal end adapted for communication with the vitreal cavity, said passageway being resiliently compressible to constrict and expand the passageway thereby to draw fluid-borne medicine from the reservoir into the passageway through said proximate end and to pump fluid-borne medicine from the passageway out of the distal end into the vitreal cavity, said outlet further including a valve for allowing fluid flow out of the reservoir but restricting flow into the reservoir.

9. The device of claim 1, wherein the reservoir includes an anteriorly facing injection port penetrable by an injection needle when the needle is forced into the port but fluid-impervious when the needle is withdrawn, and wherein the reservoir has an attachment member adjacent to the vitreal cavity at a location anteriorly of the injection port so that, when the attachment member is attached to the eyeball, movement of the reservoir is resisted when the injection needle applies force again the port.

10. The device of claim 1 wherein there is a valve in the outlet actuatable exteriorly of the body in which the eye is located, and having a dosage chamber in communication with said reservoir adapted to communicate with the vitreal cavity through the outlet, said valve being actuatable to enable a predetermined dosage of medicine to be collected in the dosage chamber and to be forced therefrom through said outlet into the vitreal cavity.

11. A device for delivering medicine into the vitreous cavity of an eye including an eyelid and an eyeball, said eye also having conjunctiva and Tenon's capsule covering the eyeball, comprising a housing having a reservoir for holding a supply of medicine, a tube having one end connected to the housing in communication with the reservoir and an opposite end, and attachment members on the housing adapted to be attached to an eyeball so that the housing and both ends of the tube are under the conjunctiva and Tenon's capsule whereby the housing and the tube are covered by the conjunctiva and Tenon's capsule, said opposite end of the tube being adapted to project through the eyeball into the vitreous cavity, the housing having wall portions surrounding the reservoir, one of said wall portions including a reservoir refiner which faces anteriorly of the eye when the housing is attached to the eyeball and which is then accessible to a refilling instrument, said refiller allowing a refilling instrument to introduce medicine through the conjunctiva and Tenon's capsule into the reservoir but preventing medicine from escaping from the reservoir.

12. The delivery device of claim 11 wherein said refiller has a predetermined marking which is capable of being visible through the conjunctiva and Tenon's capsule exteriorly of the eye when the eyelid is lifted, said marking distinguishing said refiller to facilitate its location.

13. The delivery device of claim 12 wherein said marking is a color.

14. The delivery device of claim 11 wherein the reservoir refiner is a port area of a material which is normally fluid-impervious but which can be penetrated by a sharp refilling instrument, and wherein wall portions of the housing are impenetrable to the injection instrument except for said port area.

15. The delivery device of claim 11 wherein said reservoir has an inside and an outside, wherein at least part of the wall portions of the housing is semi-permeable to minimize the pressure differential between the inside and the outside of said reservoir.

16. The device of claim 11 wherein the wall portions include a base wall and a top wall joined to the base wall, said base wall having a curvature generally complementary to the curvature of an eyeball, said top wall including a needle-penetrable and resealable port constituting said refiller, and a remainder portion, the base wall and the remainder portion of the top wall being impenetrable by an injecting needle.

17. A method of delivering medicine to the vitreous cavity of the eye comprising:

establishing a reservoir of medicine on the eyewall and under the conjunctiva, and providing a passageway joining the reservoir and the vitreous cavity and under the conjunctiva and through which medicine can move from the reservoir to the cavity, the entire reservoir and passageway being thereby under the conjunctiva.

18. The method of claim 17 including:

intermittently introducing medicine into the reservoir while the reservoir remains on the eyeball.

19. The method of claim 18, wherein the intermittent introduction of medicine involves introducing a quantity of medicine into the reservoir greater than a predetermined single dose thereof, and further enabling such a predetermined dose of medicine to move into the vitreal cavity at selected intervals between said intermittent introductions of medicine into the reservoir.

20. The method of claim 18 further involving introducing selectively different types of medicines into the reservoir at different times without removing the reservoir from the eyewall.

21. The method of claim 17 including restricting passage of medicine from the reservoir into the vitreous cavity while medicine is being introduced into the reservoir.

22. The method of claim 17 wherein the reservoir has an injection port thereon, wherein establishing the reservoir involves suturing an intravitreal medicine delivery device which includes the reservoir and the injection port on the eyewall under the conjunctiva and Tenon's capsule, said device including a fluid conductor and a pump actuatable from externally of the eye, said conductor having a proximate end connected to the reservoir and a distal end, and wherein providing the passageway further involves inserting the distal end into the vitreal cavity and subsequently actuating said pump from externally of the eye to pump fluid from the reservoir into the vitreal cavity.

* * * * *